(12) United States Patent
Crapser et al.

(10) Patent No.: US 8,573,967 B2
(45) Date of Patent: Nov. 5, 2013

(54) CANDLE ASSEMBLY AND FUEL ELEMENT THEREFOR

(75) Inventors: James R. Crapser, Racine, WI (US); Thomas A. Helf, New Berlin, WI (US); Tommy Mikic, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 12/896,600

(22) Filed: Oct. 1, 2010

(65) Prior Publication Data
US 2012/0082947 A1    Apr. 5, 2012

(51) Int. Cl.
*F23D 3/16*    (2006.01)

(52) U.S. Cl.
USPC .......................................... 431/292; 431/289

(58) Field of Classification Search
USPC .................. 431/292, 289, 301, 298
See application file for complete search history.

(56) References Cited

U.S. PATENT DOCUMENTS

| | | | |
|---|---|---|---|
| 213,184 A | 7/1879 | Frick | |
| 405,786 A | 6/1889 | Ludde | |
| 407,051 A | 7/1889 | Baumer | |
| 484,210 A | 10/1892 | Ludde | |
| 779,644 A | 1/1905 | Ferrier | |
| 837,240 A | 11/1906 | Mulkerins | |
| D43,845 S | 4/1913 | Hirschfeld | |
| 1,195,657 A | 8/1916 | Chersky | |
| 1,229,140 A | 6/1917 | Ritter | |
| 1,267,968 A | 5/1918 | Bulle | |
| 1,316,624 A | 9/1919 | Lucas | |
| 1,320,109 A | 10/1919 | Wooster | |
| 1,336,635 A | 4/1920 | Knapp | |
| 1,390,389 A | 9/1921 | Rosenfeld | |
| 1,640,734 A | 9/1927 | Smith | |
| D80,971 S | 4/1930 | Sakier | |
| D83,100 S | 1/1931 | Gisolfi | |
| D110,902 S | 8/1938 | Loesch | |
| 2,234,903 A | 3/1941 | Muench | |
| 2,237,523 A | 4/1941 | Damon | |
| 2,240,071 A | 4/1941 | Gisolfi | |
| 2,246,346 A | 6/1941 | Carroll | |

(Continued)

FOREIGN PATENT DOCUMENTS

| CA | 2208145 | 12/1998 |
|---|---|---|
| DE | 1767916 | 11/1970 |

(Continued)

OTHER PUBLICATIONS

Office Action in U.S. Appl. No. 09/742,631 dated Aug. 18, 2003.

(Continued)

*Primary Examiner* — Alfred Basichas (57) ABSTRACT

A candle assembly comprises a fuel element having a first surface, a second surface disposed opposite the first surface, and a channel extending through the fuel element from the first surface to the second surface. A support structure is adapted to support the first surface of the fuel element within a central portion of the support structure. A wick retainer has a flat portion with a centralized conduit extending outwardly from a top surface of the flat portion. A wick has a first end disposed within the wick retainer, wherein the wick and wick retainer are embedded in the fuel element prior to use such that a second end of the wick extends outwardly beyond the second surface of the fuel element.

18 Claims, 7 Drawing Sheets

(56) References Cited

U.S. PATENT DOCUMENTS

| | | |
|---|---|---|
| 2,254,906 A | 9/1941 | Petrulis |
| 2,324,753 A | 7/1943 | Alexiade |
| 2,354,343 A | 7/1944 | Webber et al. |
| 2,393,767 A | 1/1946 | Gould |
| 2,462,440 A | 2/1949 | Tierney |
| 2,713,256 A | 7/1955 | Oesterle et al. |
| 2,775,006 A | 12/1956 | Kranc |
| 2,809,512 A | 10/1957 | Hartnett |
| RE24,423 E | 2/1958 | Oesterle et al. |
| 3,121,316 A | 2/1964 | Wilson et al. |
| D206,946 S | 2/1967 | Knodt |
| D208,064 S | 7/1967 | Quistgaard et al. |
| D208,097 S | 7/1967 | Henn |
| 3,565,281 A | 2/1971 | Collie |
| 3,583,853 A | 6/1971 | Schramm |
| D226,240 S | 1/1973 | Twedt |
| 3,730,674 A | 5/1973 | Gross |
| 3,741,711 A | 6/1973 | Bryant |
| 3,749,904 A | 7/1973 | Graff |
| 3,762,857 A | 10/1973 | Andeweg |
| D229,852 S | 1/1974 | Lindbad |
| 3,790,332 A | 2/1974 | Woollard |
| 3,818,439 A | 6/1974 | Maine |
| D236,064 S | 7/1975 | Balbo |
| 3,898,039 A | 8/1975 | Lin |
| 3,910,753 A | 10/1975 | Lee |
| 3,932,113 A | 1/1976 | Thrush |
| 3,994,502 A | 11/1976 | Lombardi |
| 3,998,922 A * | 12/1976 | Weiss ........................ 264/255 |
| 4,013,397 A | 3/1977 | Neugart |
| 4,019,856 A | 4/1977 | Lacroix |
| D247,635 S | 3/1978 | Maxwell |
| D248,499 S | 7/1978 | Ulrich et al. |
| D248,500 S | 7/1978 | Ulrich et al. |
| 4,102,634 A | 7/1978 | Crisp |
| D248,787 S | 8/1978 | Ulrich et al. |
| D248,788 S | 8/1978 | Ulrich et al. |
| D248,789 S | 8/1978 | Ulrich et al. |
| D253,432 S | 11/1979 | Van Koert |
| D253,732 S | 12/1979 | Van Koert |
| 4,185,953 A | 1/1980 | Schirneker |
| 4,206,500 A | 6/1980 | Neil |
| 4,224,017 A | 9/1980 | Kayne |
| D264,385 S | 5/1982 | Meyer |
| 4,332,548 A | 6/1982 | Linton et al. |
| 4,381,914 A | 5/1983 | Ferguson |
| 4,427,366 A | 1/1984 | Moore |
| 4,477,249 A | 10/1984 | Ruzek et al. |
| 4,524,408 A | 6/1985 | Minera |
| 4,551,794 A | 11/1985 | Sandell |
| 4,557,687 A | 12/1985 | Schirneker |
| 4,568,269 A | 2/1986 | Lin |
| 4,568,270 A | 2/1986 | Marcus et al. |
| 4,588,618 A | 5/1986 | Wolfe |
| D292,525 S | 10/1987 | Van Deelen |
| 4,755,135 A | 7/1988 | Kwok |
| 4,781,895 A | 11/1988 | Spector |
| 4,804,323 A | 2/1989 | Kim |
| D312,507 S | 11/1990 | Thoreson |
| 4,983,119 A | 1/1991 | Lin |
| 5,015,175 A | 5/1991 | Lee |
| 5,069,617 A | 12/1991 | Lin |
| 5,078,591 A | 1/1992 | Despres |
| 5,078,945 A | 1/1992 | Byron |
| 5,086,380 A | 2/1992 | Hedner, Jr. |
| 5,101,328 A | 3/1992 | Hai |
| 5,174,645 A | 12/1992 | Chung |
| 5,338,187 A | 8/1994 | Elharar |
| 5,363,590 A | 11/1994 | Lee |
| D355,266 S | 2/1995 | Caplette et al. |
| 5,425,633 A | 6/1995 | Cole |
| D369,871 S | 5/1996 | Lui |
| D371,212 S | 6/1996 | Hardy et al. |
| D377,402 S | 1/1997 | Perkins |
| 5,690,484 A | 11/1997 | Leonard et al. |
| D390,676 S | 2/1998 | Hollington |
| D393,910 S | 4/1998 | Chambers et al. |
| D394,513 S | 5/1998 | Davis |
| 5,807,096 A | 9/1998 | Shin et al. |
| 5,840,246 A | 11/1998 | Hammons et al. |
| 5,842,850 A | 12/1998 | Pappas |
| D410,756 S | 6/1999 | Kleinberg |
| 5,921,767 A | 7/1999 | Song |
| 5,927,959 A | 7/1999 | Johnson |
| 5,939,005 A | 8/1999 | Materna |
| 5,951,278 A | 9/1999 | Young et al. |
| 5,955,034 A | 9/1999 | Zaunbrecher et al. |
| 5,961,318 A | 10/1999 | Chambers et al. |
| 5,961,967 A | 10/1999 | Powell et al. |
| D416,099 S | 11/1999 | Hardy |
| D416,341 S | 11/1999 | Allen |
| 5,980,241 A | 11/1999 | Schirneker |
| 6,019,804 A | 2/2000 | Requejo et al. |
| 6,033,209 A | 3/2000 | Shin et al. |
| D422,180 S | 4/2000 | Sundberg |
| 6,050,812 A | 4/2000 | Chuang |
| D425,220 S | 5/2000 | Klett et al. |
| 6,059,564 A | 5/2000 | Morris |
| 6,062,847 A | 5/2000 | Pappas |
| 6,068,472 A | 5/2000 | Freeman et al. |
| D426,902 S | 6/2000 | Hardy et al. |
| 6,074,199 A | 6/2000 | Song |
| 6,079,975 A | 6/2000 | Conover |
| 6,099,877 A | 8/2000 | Schuppan |
| D430,943 S | 9/2000 | Zutler |
| D433,168 S | 10/2000 | Cousins |
| 6,129,771 A | 10/2000 | Ficke et al. |
| 6,152,728 A | 11/2000 | Griffel |
| D436,415 S | 1/2001 | Hardy |
| 6,214,063 B1 | 4/2001 | DeStefano et al. |
| D443,080 S | 5/2001 | Klett et al. |
| D443,081 S | 5/2001 | Klett et al. |
| D443,082 S | 5/2001 | Klett et al. |
| 6,241,362 B1 | 6/2001 | Morrison |
| 6,241,513 B1 | 6/2001 | Jeneral |
| 6,267,584 B1 | 7/2001 | Zou |
| 6,270,339 B1 | 8/2001 | Zou |
| 6,273,710 B1 | 8/2001 | Zou |
| 6,276,925 B1 | 8/2001 | Varga |
| 6,290,489 B1 | 9/2001 | Seidler |
| D448,867 S | 10/2001 | Manocheo et al. |
| 6,296,477 B1 | 10/2001 | Lin |
| 6,299,435 B1 | 10/2001 | Freeman et al. |
| D450,395 S | 11/2001 | Bellenger |
| D450,865 S | 11/2001 | Bellenger et al. |
| 6,328,935 B1 | 12/2001 | Buccellato |
| 6,361,311 B1 | 3/2002 | Smith |
| D455,846 S | 4/2002 | Araujo |
| D456,539 S | 4/2002 | Leeds |
| 6,371,756 B1 | 4/2002 | Toohey |
| D459,498 S | 6/2002 | Araujo |
| 6,398,544 B2 | 6/2002 | Wright et al. |
| D461,916 S | 8/2002 | Araujo |
| 6,428,311 B1 | 8/2002 | Bernardo |
| 6,439,471 B2 | 8/2002 | Ehrlich et al. |
| D462,793 S | 9/2002 | Freeman et al. |
| 6,444,156 B1 | 9/2002 | Schwarz et al. |
| 6,450,802 B1 | 9/2002 | Steck |
| 6,454,561 B1 | 9/2002 | Colthar et al. |
| D464,745 S | 10/2002 | Mangini et al. |
| 6,468,071 B2 | 10/2002 | Zou |
| 6,488,494 B2 | 12/2002 | Lee |
| 6,491,516 B1 | 12/2002 | Tal et al. |
| D469,550 S | 1/2003 | Moeller |
| D469,893 S | 2/2003 | Shen |
| 6,520,770 B2 | 2/2003 | Zou |
| 6,537,063 B2 | 3/2003 | Pecoskie |
| 6,543,268 B2 | 4/2003 | Wright et al. |
| 6,544,302 B2 | 4/2003 | Berger et al. |
| 6,551,365 B2 | 4/2003 | Berger et al. |
| 6,554,448 B2 | 4/2003 | Carpenter et al. |
| D474,854 S | 5/2003 | Lam |
| 6,568,934 B1 | 5/2003 | Butler |
| 6,575,613 B2 | 6/2003 | Brown et al. |

(56) References Cited

U.S. PATENT DOCUMENTS

| | | |
|---|---|---|
| 6,579,089 B1 | 6/2003 | Iu |
| 6,592,637 B2 | 7/2003 | McGee et al. |
| 6,595,771 B2 | 7/2003 | Chu |
| 6,616,308 B2 | 9/2003 | Jensen et al. |
| D481,473 S | 10/2003 | Walsh |
| 6,630,110 B2 | 10/2003 | Urfig |
| 6,648,631 B2 | 11/2003 | Wright et al. |
| D485,624 S | 1/2004 | Kitamura |
| 6,688,880 B1 | 2/2004 | Pangle |
| 6,695,611 B2 | 2/2004 | Lee |
| 6,709,266 B2 | 3/2004 | Jensen |
| 6,730,137 B2 | 5/2004 | Pesu et al. |
| 6,733,279 B2 | 5/2004 | Thigpen et al. |
| D491,288 S | 6/2004 | Young |
| D493,548 S | 7/2004 | Goldman |
| 6,769,905 B2 | 8/2004 | Gray et al. |
| 6,780,382 B2 | 8/2004 | Furner et al. |
| 6,793,484 B2 | 9/2004 | Pesu et al. |
| 6,802,707 B2 | 10/2004 | Furner et al. |
| 6,808,388 B2 | 10/2004 | Lee |
| 6,849,240 B2 | 2/2005 | Nakatsu et al. |
| 6,857,869 B1 | 2/2005 | Sun |
| 6,863,525 B2 | 3/2005 | Byrd |
| 6,923,639 B2 | 8/2005 | Pesu et al. |
| 6,960,076 B2 | 11/2005 | Yu |
| 7,014,819 B2 | 3/2006 | Hart et al. |
| 7,229,280 B2 | 6/2007 | Kubicek et al. |
| 7,247,017 B2 | 7/2007 | Furner |
| 7,287,978 B2 | 10/2007 | Kubicek et al. |
| 7,291,187 B2 | 11/2007 | Welch et al. |
| 7,318,724 B2 | 1/2008 | Kubicek et al. |
| 7,442,036 B2 | 10/2008 | Kubicek et al. |
| 7,467,945 B2 | 12/2008 | Kubicek et al. |
| 7,524,187 B2 | 4/2009 | Kubicek et al. |
| 7,691,336 B2 | 4/2010 | Westring |
| 2001/0031438 A1 | 10/2001 | Hannington et al. |
| 2002/0093834 A1 | 7/2002 | Yu et al. |
| 2002/0102187 A1 | 8/2002 | Bellenger et al. |
| 2002/0119413 A1 | 8/2002 | Cheng |
| 2002/0127507 A1 | 9/2002 | Long |
| 2003/0027091 A1 | 2/2003 | Brandt |
| 2003/0064336 A1 | 4/2003 | Welch et al. |
| 2003/0134246 A1 | 7/2003 | Gray et al. |
| 2003/0162142 A1 | 8/2003 | Bennetts et al. |
| 2004/0009447 A1 | 1/2004 | Decker |
| 2004/0028551 A1 | 2/2004 | Kvietok et al. |
| 2004/0029061 A1 | 2/2004 | Dibnah et al. |
| 2004/0033171 A1 | 2/2004 | Kvietok et al. |
| 2004/0033463 A1 | 2/2004 | Pesu et al. |
| 2004/0128879 A1 | 7/2004 | Lu |
| 2004/0160764 A1 | 8/2004 | Lee |
| 2004/0229180 A1 | 11/2004 | Furner |
| 2004/0265164 A1 | 12/2004 | Woo et al. |
| 2005/0037306 A1 | 2/2005 | Nakatsu |
| 2006/0057522 A1* | 3/2006 | Kubicek et al. ............... 431/289 |
| 2006/0084021 A1 | 4/2006 | Kubicek |
| 2006/0183065 A1 | 8/2006 | Konkle, Jr. |
| 2007/0026352 A1 | 2/2007 | Kubicek et al. |

FOREIGN PATENT DOCUMENTS

| | | |
|---|---|---|
| DE | 3302591 A1 | 8/1984 |
| DE | 3335146 A1 | 4/1985 |
| DE | 3403604 A1 | 8/1985 |
| DE | 4203644 A1 | 8/1993 |
| DE | 4241292 A1 | 6/1994 |
| DE | 4314122 A1 | 11/1994 |
| DE | 19508962 A1 | 9/1996 |
| DE | 19548958 C1 | 12/1996 |
| DE | 102004011919 B3 | 6/2005 |
| EP | 0018839 A1 | 11/1980 |
| EP | 0146247 A2 | 6/1985 |
| EP | 1054054 A1 | 11/2000 |
| EP | 1336799 A2 | 8/2003 |
| FR | 2628825 A1 | 9/1989 |
| GB | 161342 | 10/1920 |
| GB | 1514338 | 6/1978 |
| GB | 2080514 A | 2/1982 |
| GB | 2239942 A | 7/1991 |
| JP | 362220594 | 9/1987 |
| JP | 406212189 | 8/1994 |
| JP | 408185710 | 7/1996 |
| WO | WO 89/06141 A1 | 7/1989 |
| WO | WO 95/12783 A1 | 5/1995 |
| WO | WO 96/02794 | 2/1996 |
| WO | WO 99/17055 | 4/1999 |
| WO | WO 99/45322 | 9/1999 |
| WO | WO 01/46618 A1 | 6/2001 |
| WO | WO 2004/008026 A1 | 1/2004 |
| WO | WO 2004/083349 A2 | 9/2004 |
| WO | WO 2004/083718 A1 | 9/2004 |
| WO | WO 2004/090417 A1 | 10/2004 |
| WO | 2006031669 A2 | 3/2006 |
| WO | 2009152504 A1 | 12/2009 |

OTHER PUBLICATIONS

Office Action in U.S. Appl. No. 09/747,525 dated Oct. 1, 2001.
Office Action in U.S. Appl. No. 09/747,525 dated Jul. 2, 2002.
Office Action in U.S. Appl. No. 09/747,525 dated Sep. 9, 2003.
Office Action in U.S. Appl. No. 09/747,525 dated Jan. 10, 2003.
Office Action in U.S. Appl. No. 09/747,525 dated May 20, 2003.
Office Action in U.S. Appl. No. 10/780,028 dated Oct. 18, 2005.
Office Action in U.S. Appl. No. 10/780,028 dated Apr. 11, 2006.
Office Action in U.S. Appl. No. 10/780,028 dated Oct. 4, 2006.
Office Action in U.S. Appl. No. 10/938,434 dated Jul. 17, 2006.
Office Action in U.S. Appl. No. 10/938,434 dated Nov. 20, 2006.
Office Action in U.S. Appl. No. 10/938,434 dated Sep. 21, 2007.
Office Action in U.S. Appl. No. 10/938,434 dated Jun. 11, 2008.
Office Action in U.S. Appl. No. 10/938,434 dated Nov. 12, 2008.
Office Action in U.S. Appl. No. 10/978,646 dated Aug. 3, 2006.
Office Action in U.S. Appl. No. 10/978,646 dated Jan. 9, 2007.
Office Action in U.S. Appl. No. 10/978,646 dated May 4, 2007.
Office Action in U.S. Appl. No. 10/978,646 dated Oct. 16, 2007.
Office Action in U.S. Appl. No. 10/978,646 dated Mar. 14, 2008.
Office Action in U.S. Appl. No. 10/978,744 dated Jul. 19, 2006.
Office Action in U.S. Appl. No. 10/978,744 dated Nov. 13, 2006.
Office Action in U.S. Appl. No. 11/123,372 dated Feb. 27, 2008.
Office Action in U.S. Appl. No. 11/123,372 dated May 30, 2008.
Office Action in U.S. Appl. No. 11/123,461 dated Mar. 7, 2007.
Office Action in U.S. Appl. No. 11/123,461 dated Sep. 4, 2007.
Office Action in U.S. Appl. No. 11/123,461 dated Feb. 26, 2008.
Office Action in U.S. Appl. No. 11/123,461 dated Jul. 11, 2008.
Office Action in U.S. Appl. No. 11/123,909 dated Mar. 7, 2007.
Office Action in U.S. Appl. No. 11/124,313 dated Feb. 28, 2007.
International Search Report and Written Opinion dated Jul. 27, 2006, Application No. PCT/US2005/032266.
International Search Report and Written Opinion dated Oct. 13, 2006, Application No. PCT/US2006/020218.
International Search Report and Written Opinion dated Mar. 13, 2007, Application No. PCT/US2006/042787.
International Search Report and Written Opinion dated Mar. 21, 2007, Application No. PCT/US2006/046057.
PCT/US2011/053577 International Search Report dated Apr. 3, 2013.

* cited by examiner

CANDLE ASSEMBLY AND FUEL ELEMENT THEREFOR

CROSS REFERENCE TO RELATED APPLICATIONS

Not Applicable.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates generally to candle assemblies, and more specifically to candle assemblies having a fuel element, a wick, and a wick retainer.

2. Description of the Background of the Invention

Candles and candle assemblies of all types are known in the art and have generally been focused on different varieties of votive candles, pillar candles, deep drawn candles, and melting plate candles. Some candle assemblies include a support structure or container to hold the candle wax, a wick, and optionally include a wick retainer that locates and secures the wick thereto.

More recently, melting plate candles and simmer plates have been used to provide rapid melting of a solid fuel element and/or rapid dispensing of a vaporizable material to the atmosphere. One example of a melting plate candle includes a wax fuel element, a removable wick disposed in the wax fuel element, and a heat conductive base having conductive elements. Heat from a flame at the wick is transferred to the heat conductive base, which in turn helps melt the wax fuel element at locations other than directly adjacent to the flame.

One safety concern of some candles and candle assemblies is flashover, whereby the wax reaches an unsafe temperature and causes combustion. There have previously been multiple attempts to help prevent flashover in candles and candle assemblies. One such attempt includes raising the wick sustainer off of a bottom wall of the support structure on which the fuel element, wick retainer, and wick sit such that the candle flame goes out when the level of the molten wax drops below the wick retainer, thereby cutting off fuel to the wick. Another way to prevent flashover is to crimp the sustainer tightly to the wick such that when molten wax drops below the sustainer, the wick is unable to access molten fuel and the flame is extinguished.

One disadvantage of previous candle assemblies is that such assemblies typically leave an amount of unused wax on the support structure because of the aforementioned methods to prevent flashover. Even in assemblies that do not try to prevent flashover, fuel may be left over, which leaves a negative impression on the consumer. Leftover and excess wax is an even larger problem when the support structure for the candle is reused with another single-use wax element. Leftover wax may cause unpleasant mixing when the new wax element is added to the support structure and an associated wick is lit, thereby sending fragrance from the leftover wax into the surrounding atmosphere at the same time as the fragrance being released from the actively burning wax.

SUMMARY OF THE INVENTION

In one embodiment of the invention, a candle assembly comprises a fuel element having a first surface, a second surface disposed opposite the first surface, and a channel extending through the fuel element from the first surface to the second surface. A support structure is adapted to support the first surface of the fuel element within a central portion of the support structure. A wick retainer has a flat portion with a centralized conduit extending outwardly from a top surface of the flat portion. A wick has a first end disposed within the wick retainer, wherein the wick and wick retainer are embedded in the fuel element prior to use such that a second end of the wick extends outwardly beyond the second surface of the fuel element.

In a different embodiment of the invention, a fuel system for a candle assembly comprises a fuel element having a first surface, a second surface disposed opposite the first surface, and a channel extending through the fuel element from the first surface to the second surface. A wick retainer has a flat portion with a centralized conduit extending outwardly from a top surface of the flat portion. A wick has a first end disposed within the wick retainer, wherein the wick and wick retainer are embedded in the fuel element prior to use such that a second end of the wick extends outwardly beyond the second surface of the fuel element.

In another embodiment of the invention, a method of providing a candle assembly comprises the steps of providing a support structure having a surface surrounding a depression in a central portion thereof, providing a fuel element comprised of a fuel having a volatile material therein, wherein the fuel element includes a wick retainer and a wick disposed therein, and creating a capillary path through the wick retainer such that the capillary path supplies fuel to the wick when a flame is present on the wick, thereby allowing substantially all of the fuel to be depleted.

These and other aspects of the invention will become apparent in light of the following detailed description.

DETAILED DESCRIPTION

The present invention is directed to candle assemblies for melting fuel elements and dispensing volatile materials contained therein. While the present invention may be embodied in many different forms, several specific embodiments are discussed herein with the understanding that the present invention is to be considered only as an exemplification of the principles of the invention, and it is not intended to limit the invention to the embodiments illustrated.

Further, although the fuel element may be described as having a fragrance embedded therein for dispersion thereof, the fuel element may include any volatile material that a consumer may desire to emit into an area surrounding the candle assembly. Illustratively, the types of volatile materials may be, for example, an insecticide, an insect repellant, an insect attractant, a fragrance, an aromatherapy scent, a positive fragrancing volatile material, an air-freshener, a deodorizer, or the like, and combinations thereof. Additives may be included in the volatile material, such as, for example, fragrances and/or preservatives.

Figure 1:
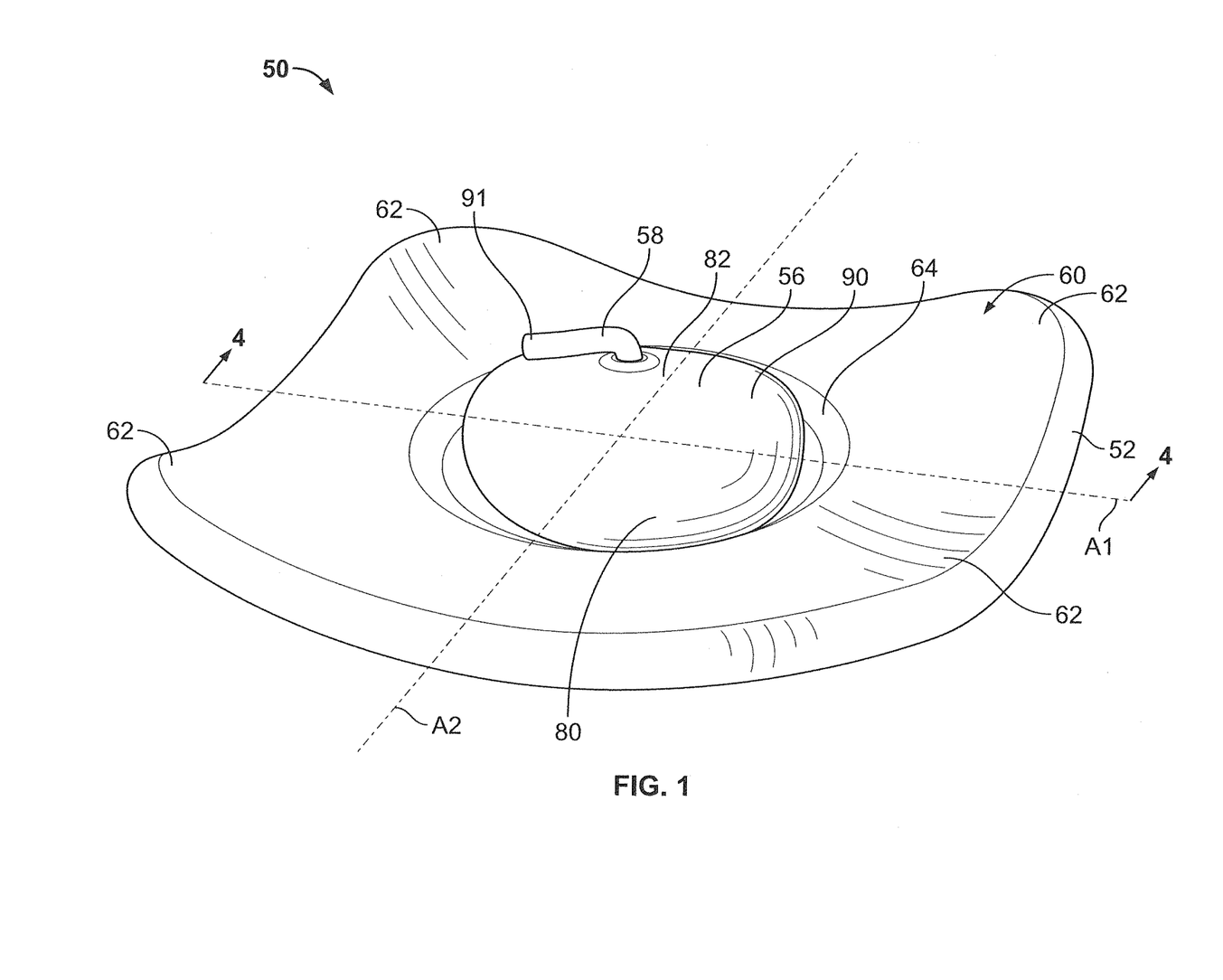
FIG. 1 illustrates a top isometric view of a candle assembly of the present invention, wherein the candle assembly includes a support plate and a fuel element, wick, and wick retainer disposed therein.
Figure 2:
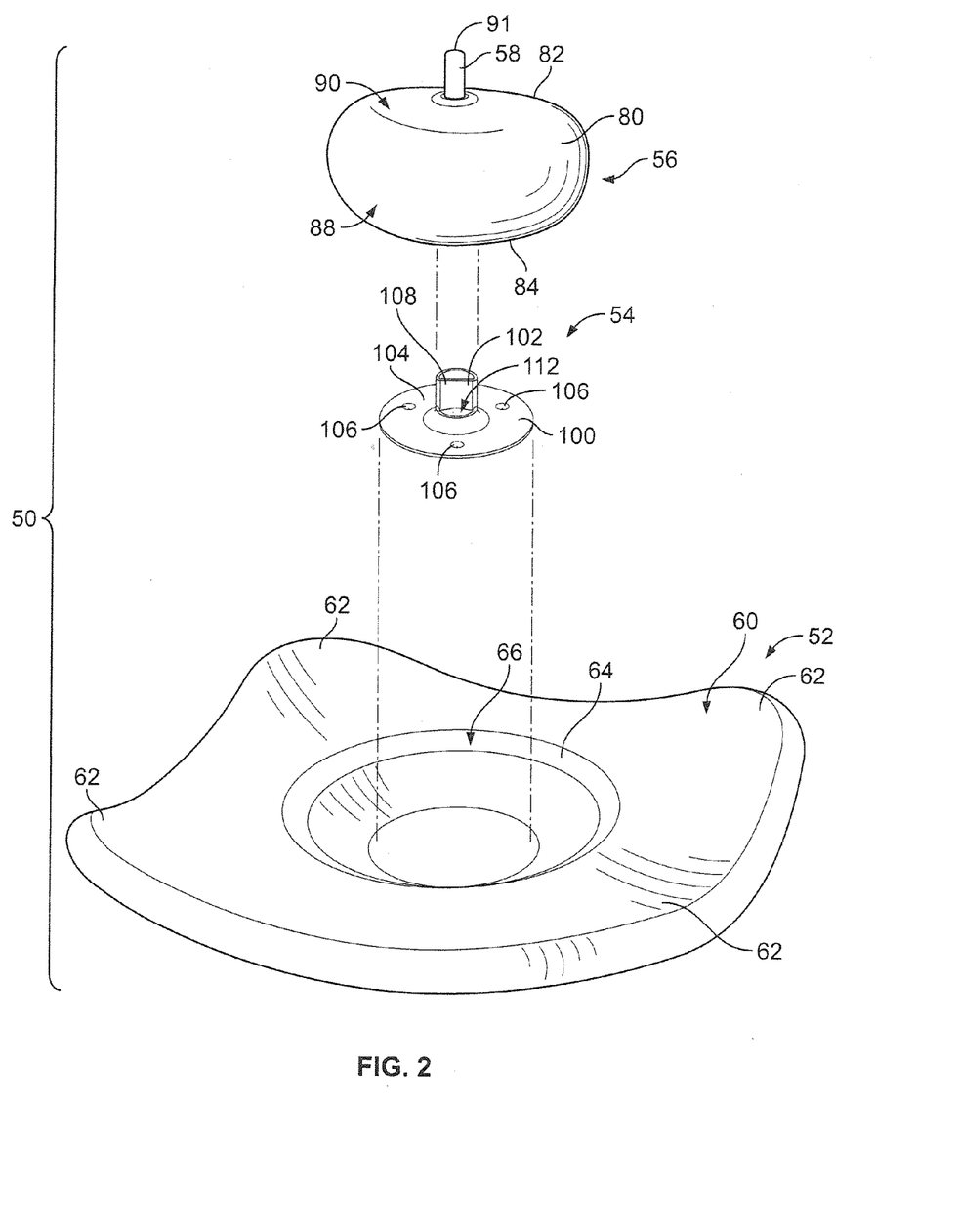
FIG. 2 illustrates an exploded top isometric view of the candle assembly of FIG. 1 further showing a wick retainer removed from the fuel element.
Figure 4:
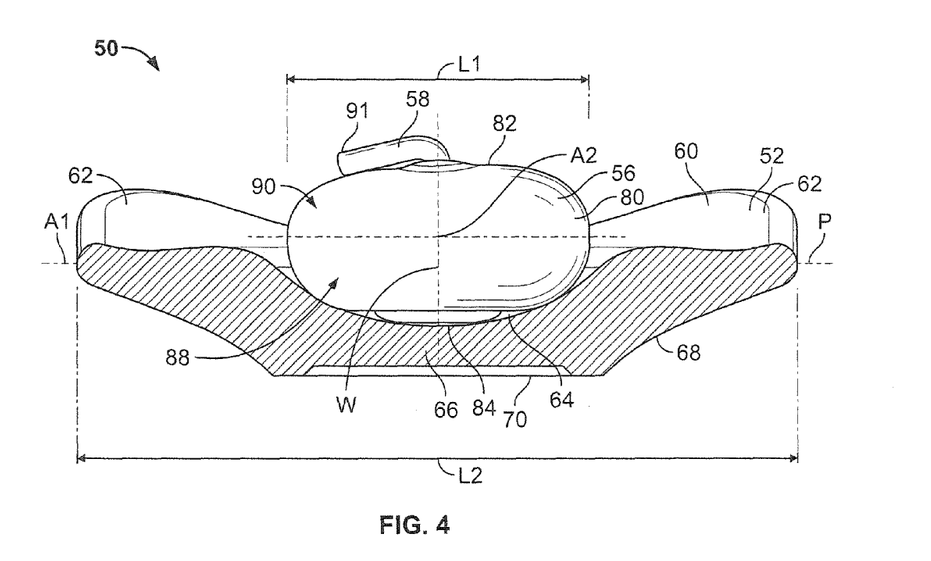
FIG. 4 is a partial cross-sectional view of the candle assembly of FIG. 1 taken along the line 4-4 of FIG. 1.

Turning now to the drawings, FIGS. 1, 2, and 4 illustrate a candle assembly 50 having a support structure in the form of a support plate 52, a wick retainer 54, a solid fuel element 56, and a wick 58. The wick retainer 54 and the wick 58 are preferably adapted to be inserted into a channel formed through the fuel element 56, as will be described in greater detail hereinafter. The fuel element 56 with the wick retainer 54 and the wick 58 disposed therein is adapted to rest on a top surface 60 of the support plate 52. In use, the wick 58 is provided with a flame that transfers heat to the surrounding fuel element 56, which provides molten fuel to effectuate combustion.

The support plate 52 has a top elevational profile that is substantially square-shaped with rounded corners and a side elevational profile that includes a generally planar top surface 60 with four upturned corners 62 at edges thereof. The top surface 60 surrounds a semi-spherical depression 64 that is disposed in a central section 66 of the support plate 52, wherein the depression 64 is adapted to support the fuel element 56. The depression 64 is shaped to contain the fuel element 56 and a pool of melted fuel. The fuel element 56 is disposed within the depression 64 so as to not contact any of the upturned corners 62. In other embodiments, the support plate 52 and/or depression 64 may take other shapes and forms so long as the fuel element 56 is disposed in a central portion of the support plate 52 and the support plate 52 and depression 64 are shaped and angled such that molten fuel travels toward the wick 58.

Figure 3:
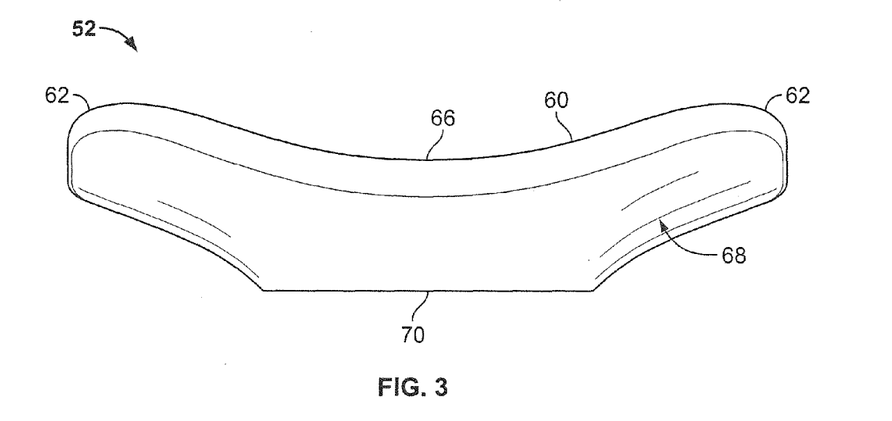
FIG. 3 is a side elevational view of the support plate of FIG. 1.

As shown in FIG. 3, the support plate 52 further includes a contoured bottom surface 68 that tapers downwardly and inwardly into a substantially flat base 70 in a central portion thereof. Preferably, the base 70 of the candle assembly 50 is flat to provide a level surface that contacts a table top or other surface to retain the candle assembly 50 in an upright and stable position.

The support plate 52 may be in the form of a tray, bowl, concave plate, or other configuration, which is capable of holding a pool of hot liquid fuel, and is shaped in one embodiment so as to funnel or channel the liquefied (e.g., melted) fuel to the wick. The support plate 52 is preferably made of a thermal insulative material, such as ceramic, clay, flame resistant plastic, and/or any other suitable thermal insulative material or combination of such materials.

Preferably, the design of the support plate incorporates a method of maintaining a pre-specified flame by having a depression designed to contain fuel that is liquefied by the flame temperature and maintains the "pool of fuel" within a pre-determined space that insures that the "liquid" will not revert back to a "solid" substance as long as heat from the flame is present. The depression 64 of the support plate 52 is contoured so as to continually control the aspect-ratio of the shrinking pool of molten fuel with respect to the flame (heat) source so that, as the fuel source is being consumed, the fuel remains molten. This pooling dynamic occurs from the beginning-to-end of the fuel supply terminating at the underside of the wick retainer 54.

Referring to FIGS. 1 and 4, the fuel element 56 is adapted to rest within the depression 64 in the top surface 60 of the support plate 52. The fuel element 56 comprises a body 80 of fuel material having the wick 58 and wick retainer 54 embedded therein. The fuel element 56 further includes an upper surface 82 and a lower surface 84 with a channel 86 extending therethrough. The channel 86 is preferably cylindrical, but may be other shapes and sizes as known in the art. The fuel element 56 preferably comprises a wax material that may be natural, synthetic, animal, and/or mixtures thereof. The wax material may also include additives and/or volatile materials as known in the art and as discussed in greater detail hereinbefore. In one embodiment, the fuel element 56 is an elongate wax puck and, in other embodiments, the fuel element 56 may have other shapes and include other meltable or flowable fuel materials having a solid or semi-solid state or otherwise maintainable in a fixed form at room temperature. The fuel element 56 may be any shape and size, but preferably is shaped to fit fully within the depression 64. As shown in FIG. 4, in one embodiment, the fuel element 56 includes a length dimension L1 that is about one third of a total length dimension L2 of the support plate 52. In another embodiment, the fuel element 56 includes a length dimension L1 that is less than about one third of the total length dimension L2 of the support plate 52. Preferably, the fuel element 56 does not cover the entirety of a surface area of the top surface 60 of the support plate 52.

The fuel element 56 is preferably designed to support a given flame height (in a liquefied state) for a specified period of time. In one embodiment, the flame height is preferably between about 0.25 inches and about 1.5 inches in height, and more preferably about 1 inch in height. Controlling the flame height within the aforementioned range provides a desirable burn-rate for aesthetics and the fragrance release.

Still referring to FIGS. 1 and 4, at least a portion of the fuel element 56 is preferably disposed below a plane P, which is defined by perpendicular axes A1, A2 that are parallel to the base 70 of the support plate 52, that extend along the planar top surface 60, and each bisect the support plate 52 into symmetrical halves. In one embodiment, approximately half, a lower half 88, of the fuel element 56, as measured by an axis running through a mid-point between the upper surface 82 and the lower surface 84 of the fuel element 56, is disposed below the plane P and an upper half 90 of the fuel element 56 is disposed about the plane P. In this embodiment, at least the upper half 90 of the fuel element 56 is preferably open to the environment and visible to a user when the candle assembly 50 is viewed from the side. A portion of the fuel element 56 extends above the highest point of the support structure 52, which in this embodiment, is the corners 62.

Figure 5:
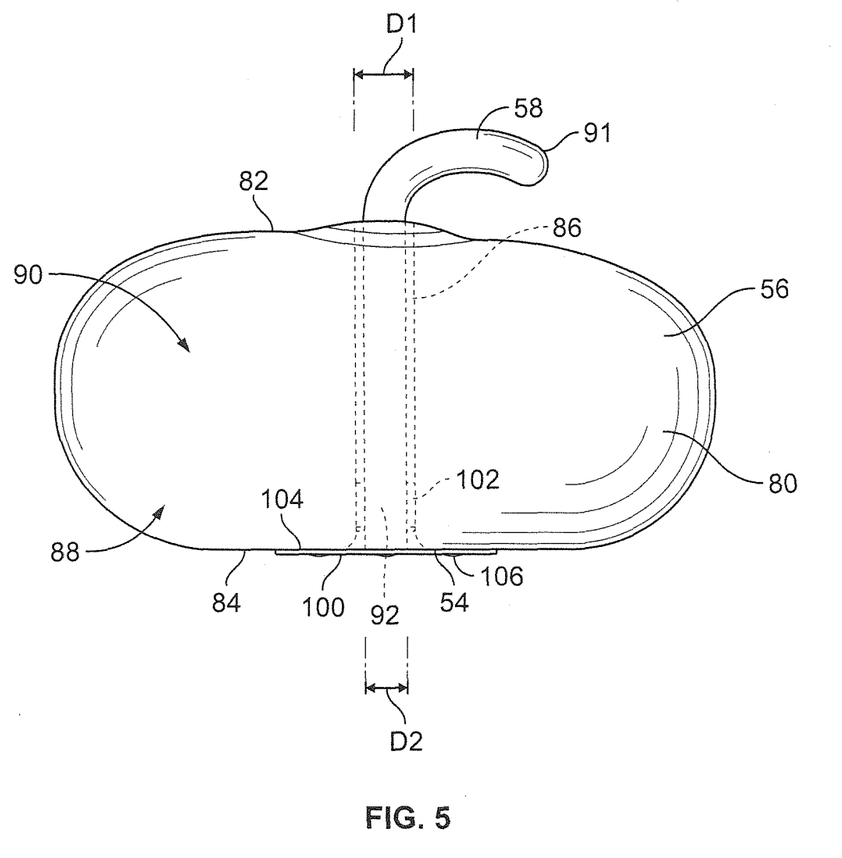
FIG. 5 is side elevational view of the fuel element of FIG. 1.

As shown in FIG. 5, the wick 58 and wick retainer 54 are preferably embedded in the fuel element 56 during the manufacturing process before the candle assembly 50 is sold such that a user is substantially unable to remove the wick retainer 54 and wick 58 from the fuel element 56 prior to use. The wick retainer 54 and the wick 58 are assembled and embedded into the fuel element 56 such that the wick 58 is disposed in the channel 86 and a first end 91 of the wick 58 extends upwardly and out of the channel 86 past the upper surface 82 of the fuel element 56. More specifically, the assembled wick retainer 54 and wick 58 are embedded in the fuel element 56 by inserting the wick 58 through the channel 86 and applying pressure to a bottom end of the wick retainer 54. As best seen in FIG. 5, a diameter D1 of the channel 86 is less than a diameter D2 of a conduit of the wick retainer 54 and, thus, when the wick retainer 54 is pushed into the fuel element 56, the wick retainer 54 becomes embedded in the wax material of the fuel element 56 due to the difference in diameters. A second end 92 of the wick 58 is connected to the wick retainer 54, as described in more detail hereinbelow.

The wick 58, in one embodiment, constitutes a conventional consumable wicking material, such as cotton, cellulose, nylon, plastic, cloth, or paper, or the like, which by capillary action carries liquid fuel to the flame. In another embodiment, non-consumable wicks may comprise such materials as porous ceramics; porous metals; fiber glass; metal fiber; compressed sand, glass, metal, or ceramic microspheres; foamed or porous glass, either natural or man-made, such as pumice or perlite; gypsum; and/or chalk.

As shown in FIGS. 5-8, the second end 92 of the wick 58 is attached to the wick retainer 54, which is adapted to support the wick 58 while at the same time allowing molten fuel to travel to the wick 58. The wick retainer 54 includes a flat circular portion 100 with a centralized conduit 102 extending upwardly from a top surface 104 thereof. The top surface 104 further includes a plurality of circular depressions 106 disposed therearound and extending downwardly therefrom. The depressions 106 are adapted to space the wick retainer 54 slightly above the top surface 60 of the support plate 52 to allow a capillary path for molten fuel to access the wick 58. Although three depressions 106 are depicted, any number of depressions 106 may be utilized, so long as the function thereof remains the same. The conduit 102 is provided in the form of a truncated cylinder 108 that, after inserting a wick 58 therein, is crimped to retain the wick 58 therein. In particular, a first side of the conduit 102 is crimped into engagement with the wick 58, whereby the first side forms a generally planar wall 109 that gives the conduit 102 a generally half-moon-shaped cross-section after crimping.

Figure 6:
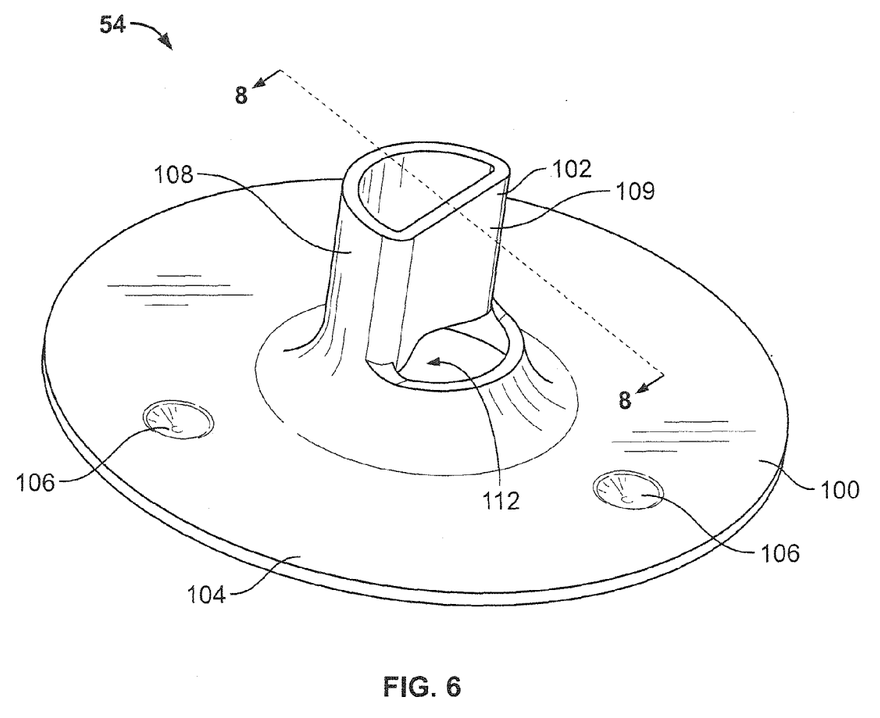
FIG. 6 is a top isometric view of the wick retainer of FIG. 2.
Figure 7:
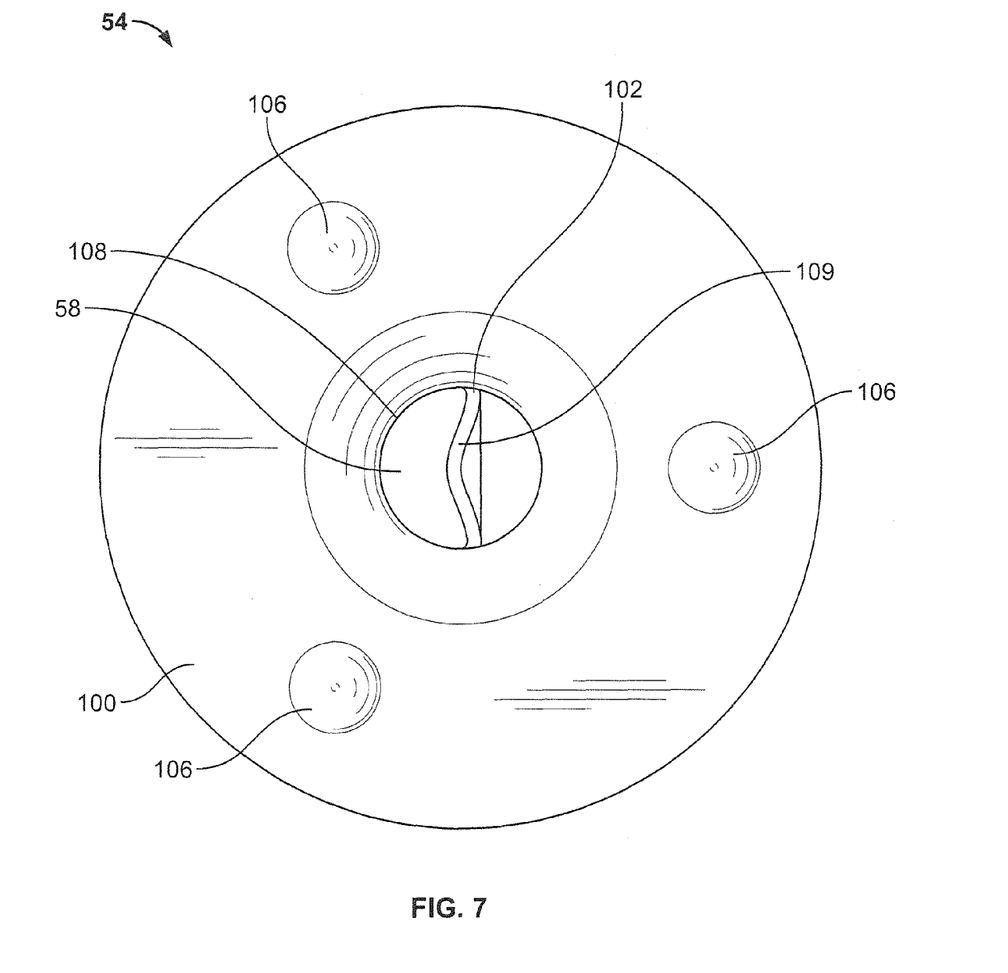
FIG. 7 is a bottom elevational view of the wick retainer of FIG. 6.
Figure 8:
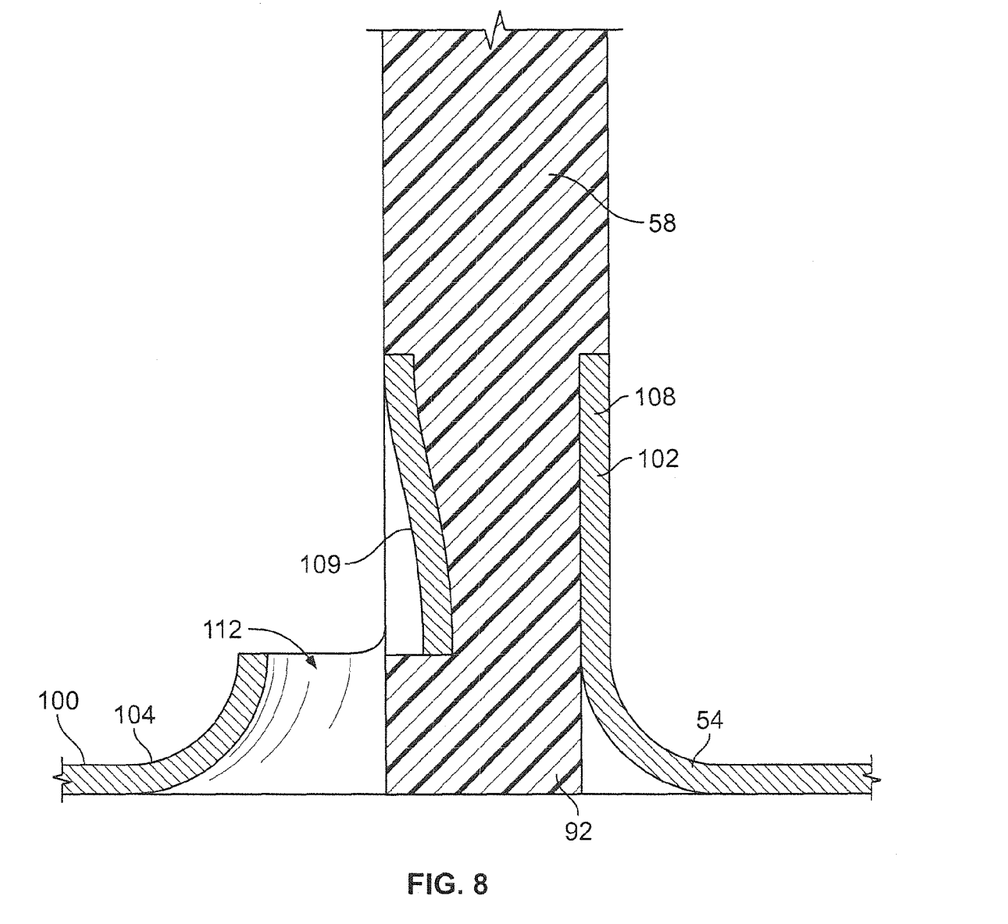
FIG. 8 is a cross-sectional view of the wick retainer of FIG. 6 with a wick disposed therein and taken generally along the lines 8-8 of FIG. 6.

As best seen in FIG. 6, the conduit 102 further includes a half-moon or oval-shaped opening 112 in the wall 109 thereof that allows molten fluid to access the second end 92 of the wick 58. The opening 112 is preferably spaced slightly above the flat portion 100 and extends inwardly such that a passageway about half of the diameter of the conduit 102 is exposed and adapted to allow molten fuel to access the wick 58. In other embodiments, the opening 112 may be different sizes and shapes so long as molten fuel is able to access the wick 58 through the opening 112. The opening 112 is preferably contoured to create a pool of liquefied fuel that resides below a lowest surface of the wick retainer 54 during use. This pool serves as the final containment point for transporting fuel to the flame and insures maximum consumption of the total pooling process which is a factor in controlling the "timed" element of the candle assembly as described in more detail hereinbelow.

In use, a user applies a flame to the wick 58, which causes wax adjacent the upper surface 82 of the fuel element 56 to melt. As the fuel element 56 melts, liquefied fuel pools around and is supplied to the wick 58 directly. As the fuel element 56 continues to burn, molten fuel collects in the depression 64 of the support plate 62 below the circular portion 100, which supplies fuel to the second end 92 of the wick 58. As the fuel element 56 burns to a point just below a top edge 130 of the wick retainer 54, liquefied fuel is also able to access the conduit 102 through the opening 112. In contrast to previous systems, the fuel of the candle assembly 50 is continuously supplied to the wick 58 until substantially all of the fuel is consumed.

In one embodiment, the candle assembly 50 described herein is used as a self-timer. Specifically, the parameters of the candle assembly 50 may be varied such that the timeframe from when the candle is lit to when all of the fuel is substantially consumed comprises a specific time period. In one embodiment, the time-frame preferably comprises between about 5 minutes and about 60 minutes and more preferably about 30 minutes. The timing aspects are apparent to the user based on the visual elements of the flame and the olfactory elements of the fragrance being released by the fuel element to deliver the prescribed period of time. The sensorial elements can be varied as can the length of time. Preferably, the fuel element for the "timed flame" can be constructed from conventional candle media.

The opportunity to reuse the support structure and experience other sensory refills presents challenges that are unique to conventional candles. These include but are not limited to controlling time, presenting a robust flame signal, and minimizing residual (fuel or fragrance) at end-of-life. The design considerations to effectuate a self-timing feature include the shape and size of the fuel elements, the shape and size of the depression for maintaining a liquefied pool of fuel thru the life of the burn, and a method for consistently transporting (virtually all) the fuel to a point of consumption. The candle assemblies 50 discussed herein further allow the user to refill the support structure from a wide selection of fuel element refills offering different colors and/or fragrances and/or timed events. The combination of parts is designed to minimize residual fuel or fragrance contamination when new and different fuel forms are introduced into the support plate.

The invention having been described in an illustrative manner, it is to be understood that the terminology used is intended to be in the nature of description rather than of limitation. The various components of the various candle assemblies described herein may be packaged as an assembled unit, as an unassembled kit including all or a portion of the components, as individual components, and in any combination thereof. Other variations, modifications, and equivalents of the present invention possible in light of the above teachings are specifically included within the scope of the impending claims.

Although directional language, such as top, bottom, upper, lower, etc., is used herein, such terminology is meant to describe the relation of components herein and not to limit the scope of the present invention. In particular, such directional language is utilized in the case that the candle assembly 50 is disposed in a use position wherein the base 70 of the support structure 52 is disposed on a surface.

We claim:

1. A candle assembly, comprising:
    a fuel element having a first surface, a second surface disposed opposite the first surface, and a channel extending through the fuel element from the first surface to the second surface;
    a support structure adapted to support the first surface of the fuel element within a depression of the support structure and wherein the second surface of the fuel element protrudes outwardly beyond the depression in a pre-operative state;
    a wick retainer having a flat portion with a centralized conduit extending outwardly from a top surface of the flat portion; and
    a wick having a first end that extends outwardly beyond the second surface of the fuel element and a second end disposed within the wick retainer, wherein the wick and wick retainer are embedded in the fuel element prior to use.

2. The candle assembly of claim 1, wherein the top surface of the flat portion of the wick retainer further includes a plurality of circular depressions disposed therearound.

3. The candle assembly of claim 1, wherein the conduit of the wick retainer is provided in the form of a truncated cylinder that, after crimping of the wick retainer with wick therein, has a generally half-moon-shaped cross-section.

4. The candle assembly of claim 1, wherein the fuel element is provided in the form of a fuel pebble that is disposed substantially entirely within the circumference of the depression in a central portion of the support structure.

5. The candle assembly of claim 1, wherein the conduit of the wick retainer further includes an opening in a surface thereof that allows molten fluid to access the second end of the wick.

6. The candle assembly of claim 5, wherein the opening is spaced slightly above the flat portion of the wick retainer.

7. The candle assembly of claim 1, wherein the support structure includes a generally planar surface surrounding the depression in a central portion thereof.

8. The candle assembly of claim 7, wherein a plurality of circular depressions is formed in the flat portion of the wick retainer such that, when the fuel element, the wick, and the wick retainer are disposed within the depression, the fuel element and the wick retainer are spaced from the surface of the depression.

9. The candle assembly of claim 8, wherein when the fuel element is placed within the depression and the fuel element is melted, the depression is shaped such that fuel from the fuel element collects adjacent the wick retainer.

10. The candle assembly of claim 9, wherein the circular depressions space the flat portion of the wick retainer from a surface of the depression such that a capillary path is created under the wick retainer, and thus under the fuel element, to supply fuel to the wick while a flame is present within the wick.

11. A fuel system for a candle assembly, comprising:
 a fuel element having a first surface, a second surface disposed opposite the first surface, and a channel extending through the fuel element from the first surface to the second surface; and
 a wick retainer having a flat portion with a centralized conduit extending outwardly from a top surface of the flat portion, wherein the conduit of the wick retainer includes an opening in a surface thereof spaced above the flat portion that allows molten fluid to access a second end of a wick, and wherein the wick has a first end that extends outwardly beyond the second surface of the fuel element and the second end is disposed within the wick retainer.

12. The fuel system of claim 11, wherein the top surface of the flat portion of the wick retainer further includes a plurality of circular depressions disposed therearound.

13. The fuel system of claim 11, wherein the conduit of the wick retainer is provided in the form of a truncated cylinder that, after crimping of the wick retainer with wick therein, has a generally half-moon-shaped cross-section.

14. The candle assembly of claim 11, wherein the opening is spaced slightly above the flat portion of the wick retainer.

15. A method of providing a candle assembly, the method comprising:
 providing a support structure having a surface surrounding a depression in a central portion thereof;
 providing a fuel element comprised of a fuel having a volatile material therein, wherein the fuel element includes a wick retainer and a wick disposed therein and wherein the fuel element includes a surface that protrudes outwardly beyond the depression;
 providing the wick retainer with a flat portion and a conduit extending outwardly from the flat portion, wherein the flat portion includes a plurality of depressions extending away from the conduit to create a first capillary path below the wick retainer when the fuel element with wick and wick retainer are disposed within the depression of the support structure; and
 creating a second capillary path through the wick retainer such that the capillary path supplies fuel to the wick when a flame is present on the wick, thereby allowing substantially all of the fuel to be depleted.

16. The method of claim 15, further including the steps of crimping the conduit of the wick retainer around the wick to retain the wick therein and creating an opening in a surface of the conduit that allows molten fluid to access the wick and forms the second capillary path.

17. The method of claim 16, wherein the first and second capillary paths provide a continuous supply of melted fuel to the wick until all of the fuel has been substantially depleted.

18. The method of claim 15, wherein the fuel element is provided in the form of a fuel pebble that is disposed substantially entirely within the circumference of the depression in the support structure.

\* \* \* \* \*